United States Patent [19]

VanLandingham

[11] 4,121,944

[45] Oct. 24, 1978

[54] PRESERVATIVE FOR BIOLOGICAL SPECIMENS

[76] Inventor: John W. VanLandingham, 3751 SW. 124 Ct., Miami, Fla. 33165

[21] Appl. No.: 650,445

[22] Filed: Jan. 19, 1976

Related U.S. Application Data

[63] Continuation of Ser. No. 312,882, Dec. 7, 1972, abandoned, which is a continuation-in-part of Ser. No. 60,649, Aug. 3, 1970, abandoned, and Ser. No. 158,136, Jun. 23, 1971, abandoned.

[51] Int. Cl.$^2$ ................................................ C08J 3/02
[52] U.S. Cl. ..................................... 106/213; 424/75; 536/111
[58] Field of Search ........................ 536/111; 106/213

[56] References Cited

U.S. PATENT DOCUMENTS

| | | | |
|---|---|---|---|
| 3,398,015 | 8/1968 | Buckler et al. | 117/118 |
| 3,563,694 | 2/1971 | Minton | 8/160 |

Primary Examiner—Melvyn I. Marquis
Attorney, Agent, or Firm—John A. Feketis

[57] ABSTRACT

A composition and process for the preservation of biological specimens in which specimens are immersed in a preservative obtained from a starch glycerite solution that has been slowly heated to a temperature above 130° C. to achieve a long-range, non-toxic preservative in which the natural color of a marine specimen can be preserved indefinitely.

12 Claims, No Drawings

PRESERVATIVE FOR BIOLOGICAL SPECIMENS

This application is a continuation of Ser. No. 312,882, filed Dec. 7, 1972, which in turn is a continuation-in-part of Ser. No. 60,649, filed Aug. 3, 1970 and Ser. No. 158,136, filed June 23, 1971, all now abandoned.

BACKGROUND OF THE INVENTION

The loss of natural color in preserved biological specimens has been a problem to biologists for quite some time, particularly to those studying marine specimens in which a plethora of colorful specimens are available from the vast spectrum of ocean inhabitants or those interested in the actual colors of plants and other biological specimens. Taking notes, recording, and photographing specimen colors for future scientific analysis is time consuming and detracts from the more specific problems in the observation of preserved specimens. Ideally, the best situation would be to preserve the natural color of the preserved marine specimen.

In the past, various preservative media have been used with varying degrees of success for the preservation of the natural color of the marine specimen, such media being usually solutions of formaldehyde and alcohol of varying concentrations. However, the solutions are generally toxic, they have an irritating odor, and they are frequently irritating or toxic to the experimenter, and therefore, difficult to work with in the laboratory and many of these preservatives cause the preserved specimen to slowly decompose.

Formaldehyde solutions continuously age with the oxidative development of formic acid. This reaction lowers the pH and is undesirable for the preservation of calcareous materials. Also, specimen color preservation has not always been of the first quality, and large volumes of the preservative have to be stored throughout the laboratory.

In biological specimens stored in formaldehyde there is a 60% destruction of the protein materials. The protein is irreversibly denatured or precipitated like egg albumin turns white when cooked.

The commonly used preservative materials are 10% formalin solutions, 40% isopropyl alcohol solutions, and 70% ethyl alcohol solutions. Formaldehyde hardens tissues. The natural appearance of the tissues with respect to color and texture is generally quickly lost and the specimen solutions become cloudy. Specimens preserved in alcohol also lose their natural color very quickly, particularly, when exposed to light.

An object of this invention is to provide an improved biological specimen preservative in which the original color of the specimen is retained over long periods of time.

Another object of this invention is to provide a preservative for biological specimens that is non-toxic and non-irritating to laboratory personnel.

Another object of this invention is to provide a preservative for biological specimens that may be used repeatedly by removing fixed specimens and dry packing them in plastic bags. Other objects will be apparent from the following specification.

I have discovered a new preservative composition, and a variety of preservative techniques and modifications of this composition that do not have the disadvantages of prior art formaldehyde and alcohol preservatives and dry packing biological specimen preservative techniques. With the use of these new preservative compositions continuous exposure to natural and artificial light caused no color deterioration in the particular specimens observed, the solutions do not become cloudy with age and the preserved specimens can be kept without being retained in the preservative solution, the solutions have indefinite shelf life, and the preserved specimen retains its original odor and skin texture.

The improved preserved biological specimens are obtained by using specifically modified starch glycerite solutions as the preservating agent. This modified product is a new composition.

The preservative effect appears to result in part from the dehydration of the specimen and the bacteriostatic action appears to be due to the development of a new reaction product obtained from the soluble starch glycerite in addition to a simple dehydration mechanism. Evidence that the preservatives are new compositions consists of the following:

1. Viscosity changes have been repetitively observed at about the same temperature (ca 130° C. during the heat treatment step used in the preparation of the preservative).

2. These viscosity changes appear to coincide with the elimination of water vapor which indicates that a condensation reaction and formation of a new compound takes place during this heat treatment step.

3. The finished product has a ketonoid odor which is not characteristic of either of the soluble starch or glycerin reactants.

4. Specimens fixed with this preservative remain well preserved years after they are removed from the preservative solution. One sample of copepods has been stored in sea water for over one year without decay. Other specimens such as plants, small fish and animal organs have also been preserved for 1 to 4 years without undergoing any deterioration.

The starting pretreated starch glycerite solutions can be prepared in the conventional manner by dissolving a soluble starch, such as potato starch, in a solvent such as a dihydric alcohol, such as ethylene glycol, diethylene glycol, propylene glycol, etc.; trihydric alcohol, such as glycerol; or low molecular weight polypropylenes having 6 to 9 carbon atoms. The preferred starches are amylopectin starch having a molecular weight of 300–3000, amylose starch having a molecular weight of 100–1000, a mixture of these starches, or a mannose, such as monosaccharidehexoses.

Raw starch is not soluble because its molecules are too large.

To make the soluble starch, add a polyol such as glycerine, to raw starch heat the mixture to 190° C., add alcohol to precipitate a product called soluble starch.

Starch glycerite is obtained by redissolving the soluble starch precipitate in glycerine by heating the mixture.

The modified starch glycerite of this invention is made by slowly redissolving the soluble starch in a polyol, such as glycerine at a redissolving-reaction temperature of about 135° C. to a temperature below the carmelization temperature. The preferred reaction temperature is between 140 to 160° C. Preferably the mixture is agitated during the redissolving-reaction step. This step is continued until it produces a colloidal solution which contains the preservative of this invention. This product has a ketonoid odor and a relatively large concentration of hydroxyl groups.

At 125° C. the viscosity of the solution increases and it looks like syrupy milk; at 130° C. the viscosity suddenly decreases significantly and a slightly turbid solution forms.

This composition is hypertonic, which means that it dehydrates biological material it comes in contact with. In cases where dehydration is undesirable, it can be reduced by dilution of the product. Since dilution may encourage the growth of bacteria, it is desirable to add a bactericide to these dilute solutions.

This colloidal solution will turn blue when subjected to an iodine indicator test which indicates that some amylodextrin is present.

An improved preservative which is a colorless solution can be made by adding about one micro liter of any mineral acid, such as phosphoric acid, to about 1000 milliliters of the colloidal product at room temperature. This acid treatment eliminates the cloudiness of the colloid solution by partially depolymerizing the carbohydrate polymers by hydrolysis and the acid acts as an antioxidant which further helps maintain the colors of biological specimens.

This clear solution does not turn blue when subjected to an iodine indicator test. Therefore the polymer product contains no starch and no amylodextrin.

The preservative solution could be further modified with one or more of the following modifiers: hydrochloric acid, sulfuric acid, sodium carbonate, acetic acid, acetic anhydride, picric acid, eugenol, menthol, any one of the monosaccharide hexoses and/or one or more of the following bacteriostats or germicides can be added to diluted solutions of the preservative; sodium benzoate, benzoic acid, sodium borate, boric acid, hexamethylenetetramine, and hydrochloric acid.

Modifiers such as those listed above, are used to alter the histochemical properties of the preservative through one or more of the following techniques:

I pH control
 A. Acid fixative generally non-clearing
 B. Basic fixative generally clearing
II Molecular weight reduction through cracking or degradation of the polymer.
III Molecular weight increase via polymerization or condensation reactions.
IV Introduction of various functional groups to promote special properties in the preservative.

The composition and techniques have been effectively used to preserve phytoplankton, zooplankton, marine crustacea, fishes up to several inches in length, scallops, sea grasses, insects, reptiles, and amphibians. The starch glycerite reaction product solution may be used to preserve any biological specimen.

Specimens are preferably injected with 100% preservative into the body cavity then immersed for 24 to 48 hours, depending upon body weight, in 75% preservative. They may be stored permanently in the 75% solution or removed and packaged dry in polyethylene bags. Color retention over long periods is generally better preserved in the solution. For small and soft bodied specimens, it is more useful to pass specimens through a concentration gradient consisting of 25%, 50%, 75% and 100% of preservative. 0.1% to 2% sodium benzoate plus 1% sodium carbonate is added to each diluted solution as a bacteriostatic in the absence of formaldehyde. 4% formaldehyde may be used as the diluent in which case most of its noxious, irritant properties seem to be thoroughly suppressed by the starch glycerite reaction product.

In a preferred embodiment of the invention the modified starch glycerite colloidal solution of this invention is prepared in the following manner:

1. Add 630 or 1260 parts/weight of a polyhydric alcohol, such as glycerin to 30 to 50 parts by weight of soluble starch powder. (Preferred ratio is 630/40 parts by weight.)
2. Heat with stirring to a temperature of 135° C to 190° C. avoiding carmelization. The preferred temperature is 150° C.
3. Optionally if 630 parts glycerine is used in step 1, when the starch powder is in solution, add an additional 630 parts by weight of glycerol and reheat to the desired temperature. Hold at this temperature for five minutes and cool to room temperature. The preservative is now ready for use.

To produce near normal turgor, the specimen may be run backwards through the concentration gradient as far as the 50% concentration. After immersion in 100% preservative for periods ranging from 24 hours to one week, depending on the particular biological specimen, the specimen may be removed from the preservative and maintained in a dry-pack container during storage. Such storage eliminates the space and cost requirement for maintaining large volumes of preservative in collections. Other advantages include the fact that preserved specimens, such as crustacea, are easier to work with (greater limberness) when preserved by this method and much greater flexibility is provided with respect to modification of the preservative for special applications. For example, the concentration may be widely varied and various additives may be used to achieve a desired effect.

EXAMPLE I

A starch glycerite reaction product solution containing 20% starch glycerite, 1% phenol, and 1% sodium benzoate was prepared in the manner described above. Fish specimens were placed in the solution. After intervals of two days, these fish were subsequently transferred to a 50% solution of the reacted starch glycerite, a 75% solution of the reacted starch glycerite, and finally a 100% solution of the reacted starch glycerite, all of these solutions contained 1% sodium benzoate as a bactericide. After 2 years, the fishes had shown no signs of color loss.

EXAMPLE II

A second example using the same starch glycerite reactant solution in the percentages of Example I, however, using 2% sodium benzoate and 0.1% hydroquinone. The same preservative technique of Example I was followed for this test. After 76 days, the fish still retained the original color.

EXAMPLE III

The same solution and amounts were used in Example III as in Example II, the only variations being the length of time the fish remained in the lower concentration. They were removed from the 20% solution after only 24 hours and placed for the same amount of time in a 50% as the 75% solution. After two years, these fish had shown no significant color loss.

EXAMPLE IV

The same starch glycerite reaction product solution used in Example III was used, but the biological specimens that were used in the solution were prepared in a different manner. For the first 24 hours, the fishes were placed in a 10% formalin solution, along with 0.1% hydroquinone, and where kept in the dark. This was to permit fixing of the fish. After 65 days the fish not only had shown no significant color loss but were not as dried out as other specimens.

EXAMPLE V

A brilliantly colored tropical fish (Royal Gramma) was fixed in a pure starch glycerite reaction product preservative (100%), then embedded in clear polyester resin. There has been no significant loss in color after months whereas similar specimens fixed in formaldehyde prior to embedding were totally discolored.

EXAMPLE VI

Larval fishes fixed with starch glycerite reactant preservative were embedded in paraffin, sectioned and stained with both Gomori Trichrome stain and hematoxylin/eosin. Upon microscopic examination, it was determined that the staining characteristics and physical condition of the cells was comparable in every way to specimens fixed with conventional preservatives.

All of the specimens in the above experiments in Examples I - VI were left in the sun as much as possible and the containers were rotated to insure uniform lighting. Specimens were kept in direct sunlight by placing them on the window sills of a laboratory. These specimens retained their color despite being exposed to sunlight which would discolor similar specimens that are preserved.

An improved embodiment of the invention comprises (a) adding 630 parts by weight of at least one polyhydric alcohol solvent to 20 to 50 parts by weight of at least one carbohydrate solute; (b) heating the mixture with stirring to a temperature of 130° C. to 175° C.; (c) adding about an additional 630 parts by weight of the solvent when the solute is in solution and reheating to a temperature between 130° C. to 175° C. for about five minutes, (d) adding at least one acid of 0.005 to 0.01 percent of the total volume to partially depolymerize and clarify the solution and to inhibit oxidation; (e) cooling the solution to between 20° C. and 27° C.; and (f) regulating the pH between 3.5 to 8.5.

The acid added in an amount of 0.0001 to 0.01 percent of the total volume to partially depolymerize and clarify the solution and to inhibit oxidation, is illustrated by the following acids:
1. Hydrochloric acid (HCL)
2. Sulfuric acid ($H_2SO_4$)
3. Phosphoric ($H_3PO_4$)
4. Acetic Acid ($CH_3 \cdot COOH$)
5. Acetic Anhydride ($CH_3CO \cdot O \cdot OC-CH_3$) Pl 6. Picric Acid The pH can be regulated between 3.5 to 8.5 by adding the necessary amount of acid a base, such as sodium carbonate or sodium benzoate.

Examples VII to X illustrate how to make the preferred depolymerized, clarified preservative solutions of this invention.

EXAMPLE VII

1. Starting with 630 parts by weight of the solvent glycerin, gradually raise the temperature while mixing.
2. Add a slurry of 20 to 50 parts (preferably 40) by weight of soluble starch powder and 40 parts by weight of glycerin (preferably at 100° C.)
3. Heat with stirring to a temperature of 130° C. to 175° C. (Preferred temperature is 150° C.).
4. When the starch powder is in solution, add an additional 590 parts by weight of glycerin and reheat to the desired temperature.
5. Adding phosphoric acid of 0.0001 to 0.01 percent of the total volume to partially depolymerize and clarify the solution and to inhibit oxidation.
6. Hold at the 150° C. temperature for an extended period of time (such as 30 minutes).
7. Cool to room temperature (preferably 20° to 27° C.).
8. Adjust the pH to 3.5 to 8.5.

EXAMPLE VIII 1000 grams of the product of Example VII was diluted with 200 grams of a diluent which contained the following ingredients:
1. Distilled water 100 parts by wt.
2. Sodium Benzoate 0.01 parts by wt.
3. Sodium Carbonate 1 parts by wt.

EXAMPLE IX 1000 grams of the product of Example VII was diluted with 150 grams of diluent which contained the following ingredients:
1. Distilled water 96 96 by volume
2. Formaldehyde 4 parts by volume Dilution of the preservative compound is sometimes necessary to control osmotic tension of the solution. Osmotic tension that is too high may cause severe shrinkage and distortions of the specimens. Dilution is necessary to provide the following functions:
1. Regulate the pH
2. Regulate the osmotic tension
3. Inhibit decomposition of the solute in the diluted solution resulting from attack by micro organisms.

The following example illustrates a preferred diluent product.

EXAMPLE X 1000 grams of the concentrated solutions prepared in Example VII is diluted with 100 grams of the following diluent:
1. Distelled water 18,000 parts by wt.
2. Sodium Citrate 5.4 parts by wt.
3. Sodium Benzoate 9 parts by wt.
4. Sodium Carbonate 9 parts by wt.
5. Distilled Chloride 155 parts by wt.

EXAMPLE XI

Specimen of *Sardinilla maderensis*
130 ± mm S.L. (Standard leyenen) G.R. - L.Br. = 110 120 (Gill Raker count in the lower range from 110 to 120.)
$p^2 = 8$ ($p^2$ identifies the pelvic fin which had 8 fin rays.)
black spot at origin of dorsal were preserved in a 100% starch glycerite reaction product solution and then reconstituted in a 50% solution. All of the fins were in very good shape. They were not too difficult to spread and count. The gill rakers were in good condition, stiffer than fresh but not as stiff as in formalin or perhaps even alcohol.

Gill filaments appeared to be very well preserved, stiffer than fresh but pliable. Scales normal. The eyes were somewhat sunken. The body was compressible (as in squeezing a hollow object) over the abdonimal cavity. Internal organs all appear (without dissection) to be in good, normal condition. The liver and other organs have retained some color.

The specimens were re-examined after about 30 hours in a 25% preservative solution. General appearance was like frozen specimens appear after thawing. There was no objectionable odor.

Fin rays were pliable and easily counted. There was some sheen remaining on the dorsal rays. They were not brittle. The gill rakers were the same as in a fresh specimen. The gill filaments looked very much like thawed frozen specimens. They were easily worked, not brittle, more yellow in color. The eyes had absorbed some liquid and were less sunken then previously. The internal organs all appeared good and normal with different colors as they should. Except for a "cavernous" feel in the middle part of the body due to dehydration, the specimen seems in very good shape and handles well.

In general biological specimens stored in 100% starch glycerite are too still to work with properly. Reconstituting in 50% or 25% appears to be necessary to eliminate this stiffness. Other than dehydration and shrinkage of the body, the extent of which must be determined by controlled testing for various specimens, parts such as fin rays, scales, bones, etc. do not seem to be affected in any way.

This preservative prevents the discoloration usually caused by contacting biological specimens with polyester resins.

Fish retains its original smell; it does not smell of formaldehyde. This preservative will also remove or nullify the formaldehyde order from formaldehyde preserved specimens by immersing the specimen in it.

What is claimed is:

1. A process of preparing a preservative composition comprising dissolving a starch in a solvent selected from the group consisting of dihydric alcohol, trihydric alcohol or a low molecular weight polypropylene and reacting this mixture at a temperature between 130° C. and a temperature below the carmelization temperature of the starch to produce a slightly turbid colloidal hypertonic reaction product which has a ketonoid odor.

2. The process of claim 1, in which said solvent is selected from the group consisting of glycerol, ethylene glycol, diethylene glycol and propylene glycol.

3. The product produced by the process of claim 1.

4. The process of claim 1, in which said solvent is glycerine.

5. The process of claim 4 in which 1260 parts by weight of glycerine are mixed with 30 to 50 parts by weight of the soluble starch and the mixture is heated to a temperature between 130° to 175° C. for about five minutes.

6. The process of claim 4, in which the soluble starch is obtained by dissolving amylopectin starch or amylose starch in glycerol solvent.

7. The product produced by the process of claim 4.

8. The process of claim 1 in which a clarifying amount of an acid is added to the slightly turbid colloidal product to produce a clear solution.

9. The product produced by the process of claim 8.

10. The process of claim 8, in which the clarifying amount of acid added to the turbid colloid is about 5 micro liters of acid per about 1000 milliliters.

11. The process of claim 8, in which the acid added is about 0.0001 to 0.01% of the total volume of the colloid.

12. The process of claim 8, in which said solution is cooled to a temperature between about 20° to 27° C. and the pH of the product is adjusted to between about 3.5 to 8.5.

* * * * *